United States Patent [19]

Fujii et al.

[11] Patent Number: 4,914,105

[45] Date of Patent: Apr. 3, 1990

[54] ANTI-CANCER COMPOSITIONS FOR DELIVERING 5-FLUOROURACIL

[76] Inventors: Setsuro Fujii, 4/27 - 131, 1-chome, Nishimidorigaoka, Toyonaka-shi, Osaka-fu; Norio Unemi, 34-14, Aza-Onishi, Tainohama, Kitajima-cho, Itano-gun, Tokushima-ken; Setsuo Takeda, 6, 6-chome, Suiketohon-cho, Tokushima-shi, Tokushima-ken, all of Japan

[21] Appl. No.: 932,516

[22] Filed: Nov. 20, 1986

Related U.S. Application Data

[60] Division of Ser. No. 552,263, Nov. 16, 1983, Pat. No. 4,650,801, which is a continuation of Ser. No. 214,021, Dec. 8, 1980, abandoned, which is a continuation-in-part of Ser. No. 21,317, Mar. 16, 1979, abandoned.

[30] Foreign Application Priority Data

| Mar. 27, 1978 | [JP] | Japan | 53-35834 |
| Jul. 28, 1978 | [JP] | Japan | 53-92813 |
| Nov. 7, 1978 | [JP] | Japan | 53-137686 |

[51] Int. Cl.⁴ .................. A61K 31/505; A61K 31/70
[52] U.S. Cl. ........................................ 514/274; 514/50
[58] Field of Search .................................. 514/274

[56] References Cited

U.S. PATENT DOCUMENTS

| 4,328,229 | 5/1982 | Fujii et al. | 424/251 |
| 4,432,348 | 2/1984 | Wakatsugawa | 514/48 |
| 4,434,788 | 3/1984 | Wakatsugawa | 514/48 |
| 4,481,203 | 11/1984 | Fujii et al. | 424/251 |
| 4,507,301 | 3/1985 | Fujii et al. | 514/274 |

OTHER PUBLICATIONS

Chemical Abstracts, 92:47236w(1980).
Fujii et al., 99412t, *Chemical Abstracts*, vol. 81, pp. 32-33, (1974).
Burchenal, J., et al., "Studies on the Synergism of Fluorinated Pyrimidines and Certain Pyrimide and Purine Derivatives Against Transplanted Mouse Leukemia", *Cancer Chemotherapy Rpts.* 6, pp. 1-5, (1960).
Jato, J. et al., "5-Fluorouracial and Derivatives in Cancer Chemotheraphy III", *Journal of Pharmaceutical Sciences*, vol. 62, No. 12, pp. 1975-1977, (1973).
Jato, J., et al., "Effect of Deoxyuridine Coadministration on Toxicity and Antitumor Activity of Fluorouracil and Floxuridine", *Journal of Pharmaceutical Sciences*, vol. 64, No. 6, pp. 943-946, (1975).

*Primary Examiner*—Jerome D. Goldberg
*Attorney, Agent, or Firm*—Armstrong, Nikaido, Marmelstein, Kubovcik & Murray

[57] ABSTRACT

An anti-cancer composition which comprises at least one 5-fluorouracil derivative, and a uracil derivative.

8 Claims, No Drawings

ANTI-CANCER COMPOSITIONS FOR DELIVERING 5-FLUOROURACIL

This is a divisional application of Ser. No. 552,263, filed Nov. 16, 1983, now U.S. Pat. No. 4,650,801; which is a continuation of Ser. No. 214,021 filed Dec. 8, 1980, now abandoned; which in turn, is a continuation-in-part of Ser. No. 21,317, filed Mar. 16, 1979, now abandoned.

This invention relates to anti-cancer compositions.

Extensive research on the chemotherapy of cancers has heretofore been conducted, with the chemotherapy of cancers commenced in the latter half of the 1940's for the control of nucleic acid metabolism. As antimetabolites to nucleic acids, 6-mercaptopurine was synthesized first, followed by the discover of 5-fluorouracil.

5-Fluorouracil was synthesized by Duschinsky in 1957 and found to have anticancer activity by Heidelberger et al. The compound has a wide anti-cancer spectrum range, produces outstanding effects especially on adenocarcinomas and is therefore one of the anti-cancer agents which are most widely used for clinical purposes. Since 5-fluorouracil is typical of antagonists to nucleic acid metabolism, intensive research is still continued on compounds having 5-fluorouracil as the basic skeleton. Recently reports have been made on several excellent compounds including, for example, 1-(2-tetrahydrofuryl)-5-fluorouracil developed in the Soviet Union as a masked-type compound of 5-fluorouracil. This compound is slowly converted to 5-fluorouracil. This compound is slowly converted to 5-fluorouracil in vivo almost without producing the direct toxic effect that would result from the administration of 5-fluorouracil. Thus the method has been established in Japan of using the compound for therapy as an oral anti-cancer agent. The compound nevertheless is said to be somewhat inferior to 5-fluorouracil in efficacy, so that it is desired to develop 5-fluorouracil derivatives having still higher anti-cancer activity and reduced side effects which are therapeutically justifiable.

1-(2-Tetrahydrofuryl)-5-fluorouracil is of significant value because it is usable with little or no direct side effect as mentioned above; for example, it can be orally given with a reduced influence on the digestive system. However, the compound still remains to be improved in its anti-cancer effects. While it is generally believed that the derivatives having 5-fluorouracil as the basic skeleton thereof exhibit an anti-cancer effect when converted to 5-fluorouracil in vivo, the insufficient effect observed appears attributable partly to the fact that the resulting 5-fluorouracil is further decomposed and become inactive. For reference, it is said that when 5-fluorouracil is intravenously given, the concentration of the compound in the blood reduces to one-half the initial value in about 15 to about 20 minutes. Shimoyama et al. have suggested that the effects of antimetabolites such as 5-fluorouracil are time-dependent, stating that it is desirable to maintain the antimetabolite at a specific concentration in cancer tissues for a prolonged period of time. It therefore follows that in order to enable 5-fluorouracil derivatives to achieve an improved anti-cancer effect, there is the necessity of impeding the decomposition and inactivation of 5-fluorouracil converted from the derivative in the living body. The result will be more preferable if this can be realized more peculiarly in cancer tissues than in normal tissues. From this viewpoint, we carried out intensive research and found that the foregoing problem could be overcome by the use of a 5-fluorouracil conjointly with uracil. We have already filed patent applications in many countries based on this finding.

We have further conducted continued research in an attempt to obtain anti-cancer compositions permitting 5-fluorouracils to exhibit an enhanced anti-cancer effect and found that the contemplated object can be fulfilled also by the use of a 5-fluorouracil conjointly with a specific compound.

An object of this invention is to provide an anti-cancer composition which contains a 5-fluorouracil and which enables the 5-fluorouracil to produce an outstanding anti-cancer effect by inhibiting the decomposition and inactivation of 5-fluorouracil converted from the 5-fluorouracil component in vivo.

Another object of this invention is to provide an anti-cancer composition containing a 5-fluorouracil and having a high anti-cancer effect, suppressed toxicity and reduced side effects.

The present invention provides anti-cancer compositions for delivering 5-fluorouracil to cancer tissues in warm-blooded animals, the compositions comprising a pharmaceutically effective amount of at least one 5-fluorouracil (a) and an effective amount of a uracil derivative (b), the 5-fluorouracil (a) being represented by the formula

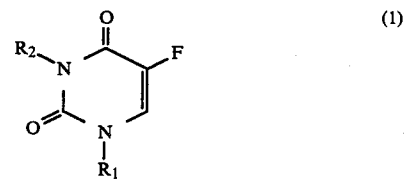

(1)

wherein $R_1$ and $R_2$ are the same or different and are each hydrogen, alkoxymethyl having 2 to 7 carbon atoms, tetrahydrofuryl or alkylcarbamoyl having 2 to 9 carbon atoms, and the uracil derivative (b) being a compound selected from the group consisting of cytosine, cytidine, 2'-deoxycytidine and compounds represented by the formula

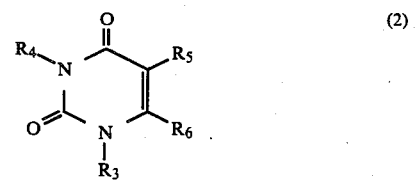

(2)

wherein $R_3$ is hydrogen, acetyl, 2-tetrahydrofuryl, hexylcarbamoyl, cyclohexylcarbamoyl or sugar residue, $R_4$ is hydrogen or benzoyl, $R_5$ is hydrogen, methyl, bromine or iodine, and $R_6$ is hydrogen or carboxyl.

Although the uracil derivative useful in this invention has little or no anti-cancer effect in itself, the conjoint use of the derivative and the 5-fluorouracil produces a greatly enhanced anti-cancer effect and achieves a remarkably improved therapeutic result.

The 5-fluorouracils useful in this invention are a wide variety of compounds represented by the formula (1). The groups $R_1$ and $R_2$ thereof include alkoxymethyl groups, having 2 to 7 carbon atoms, such as ethoxymethyl, butoxymethyl and hexyloxymethyl, and alkylcarbamoyl groups, having 2 to 9 carbon atoms, such as ethylcarbamoyl, butylcarbamoyl, hexylcarbamoyl and octylcarbamoyl.

Typical of the compounds of the formula (1) are given below.
5-Fluorouracil (Compound 1)
1-Methoxymethyl-5fluorouracil (Compound 2)
1-Ethoxymethyl-5-fluorouracil (Compound 3)
1,3-bis(Ethoxymethyl)-5-fluorouracil (Compound 4)
1-(2-Tetrahydrofuryl)-5-fluorouracil (Compound 5)
3-(2-Tetrahydrofuryl)-5-fluorouracil (Compound 6)
1,3-bis(2-Tetrahydrofuryl)-5-fluorouracil (Compound 7)
1-Ethylcarbamoyl-5-fluorouracil (Compound 8)
1-Isopropylcarbamoyl-5-fluorouracil (Compound 9)
1-n-Butylcarbamoyl-5-fluorouracil (Compound 10)
1-n-Hexylcarbamoyl-5-fluorouracil (Compound 11)

5-Fluorouracil derivatives other than those represented by the formula (1) will similarly be converted to 5-fluorouracil in vivo, presumably giving an increased anti-cancer effect when used conjointly with the above-specified uracil derivative (b).

The compounds of the formula (1) are already known. For example, Compound 1 is disclosed in Japanese Published Examined Patent Application No. 3873/1961, Compound 3 in Japanese Published Unexamined Patent Application No. 37787/1975, Compound 5 in Japanese Published Examined Patent Application No. 10510/1974, Compound 6 in Japanese Published Unexamined Patent Application No. 51373/1977, Compound 7 in Japanese Published Unexamined Patent Application No. 50384/1975 and Compound 11 in Japanese Published Unexamined Patent Application No. 148365/1975.

Typical of useful uracil derivatives (b) are cytosine, cytidine, 2′-deoxycytidine and compounds represented by the formula

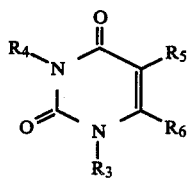

(2)

wherein $R_3$ is hydrogen, acetyl, 2-tetrahydrofuryl, hexylcarbamoyl, cyclohexylcarbamoyl or sugar residue, $R_4$ is hydrogen or benzoyl, $R_5$ is hydrogen, methyl, bromine or iodine, and $R_6$ is hydrogen or carboxyl.

The proportions of the 5-fluorouracil and the uracil derivative to be used for preparing the anti-cancer compositions of this invention are not specifically limited but variable depending on the kinds of these compounds. Generally it is preferable to use about 0.5 to 20 moles of the latter per mole of the former.

The anti-cancer compositions of this invention comprising a 5-fluorouracil and a uracil derivative are useful for curing cancers in warm-blooded animals. When the 5-fluorouracil component is converted to 5-fluorouracil in vivo, the presence of the uracil derivative suppresses the decomposition and inactivation of the resulting 5-fluorouracil, consequently permitting the composition to produce an outstanding anti-cancer effect. According to this invention, the 5-fluorouracil (a) and uracil derivative (b) can be administered to warm-blooded animals individually in separate doses but are given preferably at the same time in the form of a single preparation. The anti-cancer compositions of this invention can be administered in the desired form of preparation in accordance with the therapy contemplated. They are provided for example as tablets, capsules and granules for oral administration or as parenteral solutions and suppositories for non-oral administration. These preparations can be formulated with use of carriers already known in the art.

Examples of useful carriers for making oral preparations are lactose, sucrose, starch, talc, magnesium stearate, crystalline cellulose, methyl cellulose, hydroxypropyl cellulose, hydroxypropylmethyl cellulose, carboxymethyl cellulose, glycerin, sodium alginate, gum arabic, etc. The amount of the 5-fluorouracil (a) in the oral preparations may preferably be 10 to 200 mg per dosage unit. Carriers suitable for parenteral preparations are, for example, water, physiological saline solution, etc., which can be used with tris(hydroxymethyl)-aminomethane, sodium carbonate, sodium hydroxide or the like serving as a solubilizer or pH adjusting agent. The parenteral preparations contain preferably 50 to 1,000 mg of the 5-fluorouracil (a) per dosage unit. Suitable carriers for preparing suppositories are, for example, cacao butter, Witepsol-W35 (fat, trade mark of Dynamit Nobel A. G. of Germany). The suppositories may contain preferably 250 to 1,000 mg of the 5-fluorouracil (a) per piece. The daily dose of the present composition is not specifically limited but can be varied with the kind of the 5-fluorouracil as well as of the uracil derivative. The results of clinical applications and potency tests appear to indicate that preferred doses are usually about 20 to about 1,200 mg for oral operations, about 50 to about 2,000 mg for parenteral solutions and about 250 to about 2,000 mg for suppositories, all calculated as 5-fluorouracils.

PREPARATION 1

| Preparation | |
|---|---|
| Compound 6 | 25 mg |
| 1-(2-Tetrahydrofuryl)uracil | 200 mg |
| Lactose | 172 mg |
| Magnesium stearate | 3 mg |
| | 400 mg (per capsule) |

An encapsulated preparation is formulated from the above ingredients.

PREPARATION 2

| Preparation | |
|---|---|
| Compound 5 | 100 mg |
| 3-Benzoyluracil | 150 mg |
| Sodium carbonate | 440 mg |
| Sodium hydroxide | 35 mg |
| Distilled water | (suitable amount) |
| | 10 ml (per ampule) |

A parenteral solution is prepared from the above ingredients.

The anti-cancer compositions of this invention are tested in mice by the following methods to determine acute toxicity, anti-cancer effect and therapeutic index.

(a) Acute toxicity

Male mice of ICR strain weighing 22±1 g are used, 5 mice in each group. A 5-fluorouracil (a) and uracil derivative (b) in the proportions listed in Tables 1-16 are suspended in a 5% solution of gum arabic to prepare a suspension, which is forcibly orally administered to each mouse through a tube at a dose of 1 ml/100 g. Over the following period of three weeks the mice are checked every day for poisoning, body weight and mortality. The $LD_{50}$ is determined according to the up-and-down method 3 weeks after the administration. The results are given in Table 1.

(b) Anti-cancer effect

Tissues of sarcoma 180, $2 \times 10^6$, are subcutaneously transplanted in the back of male mice of ICR strain (6 mice in each group). A 5-fluorouracil (a) and uracil derivative (b) in the proportions listed in Table 1 are suspended in a 5% solution of gum arabic to prepare a suspension. Twenty-four hours after the transplantation and during the following seven consecutive days the suspension is orally given to the animal once every day. On the 10th day after the transplantation, the tumor is removed from the body and weighed to calculate the average weight (T) of the tumors in the group to which the composition has been given and the corresponding weight (C) in the control group to determine the ratio T/C. The effective dose ($ED_{50}$) for achieving 50% cancer inhibition is determined from the dose-response curve involving the dose and effect (T/C). The results are given in Table 1.

(c) Therapeutic index

The $LD_{50}$ and $ED_{50}$ values obtained above are used to determine the therapeutic index ($LD_{50}/ED_{50}$). The results are also listed in Table 1.

TABLE 1

| 5-Fluorouracil (a) (Compd. No.) | (b) = 3-Benzoyluracil | | | Therapeutic Index ($LD_{50}/ED_{50}$) |
|---|---|---|---|---|
| | (b)/(a) mol ratio | $LD_{50}$ (mg/kg) | $ED_{50}$ (mg/kg) | |
| 1 | 0 | 130 | 24 | 5.4 |
| | 1 | 120 | 18 | 6.7 |
| | 2 | 96 | 12 | 8.0 |
| | 10 | 71 | 9 | 7.9 |
| 5 | 0 | 820 | 140 | 5.9 |
| | 1 | 746 | 98 | 7.6 |
| | 2 | 621 | 37 | 16.8 |
| | 10 | 509 | 30 | 17.0 |
| 7 | 0 | 2224 | 118 | 18.8 |
| | 1 | 1839 | 68 | 27.0 |
| | 2 | 1263 | 49 | 25.8 |
| | 10 | 764 | 23 | 33.2 |
| 11 | 0 | 1260 | 60 | 21.0 |
| | 1 | 1180 | 45 | 26.2 |
| | 2 | 944 | 27 | 35.0 |
| | 10 | 688 | 22 | 31.3 |
| 3 | 0 | 1000 | 112 | 8.9 |

TABLE 1-continued

| 5-Fluorouracil (a) (Compd. No.) | (b) = 3-Benzoyluracil | | | Therapeutic Index ($LD_{50}/ED_{50}$) |
|---|---|---|---|---|
| | (b)/(a) mol ratio | $LD_{50}$ (mg/kg) | $ED_{50}$ (mg/kg) | |
| | 1 | 900 | 78 | 11.5 |
| | 2 | 549 | 33 | 16.6 |
| | 10 | 311 | 24 | 13.0 |
| 6 | 0 | 1021 | 73 | 13.1 |
| | 1 | 768 | 42 | 18.3 |
| | 2 | 663 | 32 | 20.7 |
| | 10 | 448 | 25 | 17.9 |

Variations of the concentration of 5-fluorouracil in the cancer cellular tissue with the lapse of time are determined by the following method when the 5-fluorouracil derivative (a) is administered to rats having cancer:

$^3$H-FT-207(300 $\mu$Ci/Kg) or $^3$H-FD-1(300 $\mu$Ci/Kg) with cytosine, cytidine or 2'-deoxycytidine were suspended in 5% acasia solution and administered orally to AH 130 bearing rats through a stomach tube, each of 3 rats/group. FT-207 is 1-(2-tetrahydrofuryl)-5-fluorouracil and FD-1 is 1,3-bis(2-tetrahydrofuryl)-5-fluorouracil. The rat were sacrified at various periods, the tumors were removed and used for analysis. Tumor were homogenized in a equal volume of saline, 1.0 ml of each sample was suspended in 7 volumes of cold methanol and centrifuged at 3000 rpm for 10 min. The precipitate was washed twice with 2 volumes of cold methanol and the mixture was centrifuged. The supernatant was combined with first supernatant and dried under nitrogen. The dried material was dissolved in 100 $\mu$l of 50% methanol and an aliquot (10 $\mu$l) was applied to thin layer chromatography (TLC) plate (TLC plate: Kieselgel 60 F254 pre-coated, $2 \times 20$ cm, thickness 0.25 mm, Merck) beforehand carrier FT-207, FD-1 and 5-fluorouracil (5-FU) were applied, and developed in a solvent composed of chloroform:ethylacetate (1:9 V/V). After development, the spot of 5-FU(Rf 0.20) was separated from FT-207 (Rf 0.47) and FD-1(Rf 0.64), and 5-FU fraction was scraped off, placed in a vial and extracted with 0.2 ml of methanol for 2 hr. Samples were mixed with 10 ml of scintillator containing 4 g of 2,5-diphenyloxazole, 0.4 g of 1,4-bis[2-(4-methyl-5-phenyloxazolyl)]benzene and 100 g of naphthalene per liter of solvent composed of dioxane:toluene:ethylcellosolve=15:3:2 (v/v/v), and the radio activity was measured with Aloka LSC 673 liquid scintillation spectrometor. Test results with each alone administration of FT-207, FD-1, cytosine, cytidine and 2'-deoxycytidine are also shown in Table 2 below.

TABLE 2

| Component and dosage (m.mol/Kg) | | | mole ratio | Concentration of 5-FU ($\mu$g/ml) in cancer tissues | | | |
|---|---|---|---|---|---|---|---|
| | | | | 1 hr | 2 hr | 4 hr | 8 hr |
| FT-207 0.075 | Cytosine | 0.0375 | 1:0.5 | 0.067 | 0.068 | 0.053 | 0.040 |
| | | 0.75 | 1:10 | 0.087 | 0.089 | 0.129 | 0.123 |
| | | 1.5 | 1:20 | 0.113 | 0.112 | 0.180 | 0.144 |
| | Cytidine | 0.0375 | 1:0.5 | 0.059 | 0.067 | 0.053 | 0.041 |
| | | 0.75 | 1:10 | 0.081 | 0.106 | 0.091 | 0.082 |
| | | 1.5 | 1:20 | 0.087 | 0.089 | 0.155 | 0.086 |
| | 2'-Deoxycytidine | 0.0375 | 1:0.5 | 0.070 | 0.057 | 0.041 | 0.038 |
| | | 0.75 | 1:10 | 0.080 | 0.097 | 0.087 | 0.080 |
| | | 1.5 | 1:20 | 0.083 | 0.081 | 0.112 | 0.088 |
| FD-1 0.0185 | Cytosine | 0.00925 | 1:0.5 | 0.041 | 0.035 | 0.019 | 0.011 |
| | | 0.185 | 1:10 | 0.091 | 0.061 | 0.035 | 0.021 |
| | | 0.375 | 1:20 | 0.101 | 0.067 | 0.038 | 0.023 |
| | Cytidine | 0.00925 | 1:0.5 | 0.042 | 0.031 | 0.014 | 0.010 |
| | | 0.185 | 1:10 | 0.096 | 0.068 | 0.059 | 0.038 |

TABLE 2-continued

| Component and dosage (m.mol/Kg) | | mole ratio | Concentration of 5-FU (μg/ml) in cancer tissues | | | |
|---|---|---|---|---|---|---|
| | | | 1 hr | 2 hr | 4 hr | 8 hr |
| | 0.375 | 1:20 | 0.091 | 0.101 | 0.035 | 0.033 |
| 2'-Deoxycytidine | 0.00925 | 1:0.5 | 0.040 | 0.033 | 0.017 | 0.008 |
| | 0.185 | 1:10 | 0.073 | 0.062 | 0.049 | 0.025 |
| | 0.375 | 1:20 | 0.073 | 0.059 | 0.041 | 0.024 |
| FT-207 0.075 alone | | — | 0.049 | 0.044 | 0.021 | 0.019 |
| FD-1 0.0185 alone | | — | 0.033 | 0.024 | 0.011 | 0.008 |
| Cytosine 1.5 alone | | — | 0.000 | 0.000 | 0.000 | 0.000 |
| Cytidine 1.5 alone | | — | 0.000 | 0.000 | 0.000 | 0.000 |
| 2'-Deoxycytidine 1.5 alone | | — | 0.000 | 0.000 | 0.000 | 0.000 |

As will be appreciated from the 5-fluorouracil concentration values reported hereinabove, the anti-cancer composition of the present invention functions in the manner of a prodrug. That is, the 5-fluorouracil derivative (a) such as 1-(2-tetrahydrofuryl)-5-fluorouracil and 1,3-bis(2-tetrahydrofuryl)-5-fluorouracil in the anti-cancer composition of the present invention is converted in the body into 5-fluorouracil. The concentration of 5-fluorouracil maintained in the cancer cellular tissue of test animals for a prolonged period of time is much higher when the 5-fluorouracil derivative (a) is administered with uracil derivative (b) such as cytosine, cytidine or 2'-deoxycytidine than when the 5-fluorouracil derivative (a) is administered alone. The composition of the present invention thus functions as a delivery system for delivering 5-fluorouracil to a cancer in a patient. The cancers which respond to the present treatment are those cancers which are sensitive to 5-fluorouracil therapy. Thus, as will be clear from the values reported in Table 2 hereinabove, cancers sensitive to 5-fluorouracil therapy are treated by administering to a patient having such cancer an effective amount of the 5-fluorouracil derivative, together with uracil derivative and a pharmaceutical excipient. The excipient is, preferably, sterile.

As know to those in the art, the cancers which are sensitive to 5-fluorouracil therapy include breast cancer, cancer of the esophagus, lung cancer, liver cancer and cancers of the gastro-intestinal system, such as stomach cancer, cancers of the intestines, cancer of the rectum, and the like.

We claim:

1. An anti-cancer composition for delivering 5-fluorouracil to cancer tissues sensitive to 5-fluorouracil in warm-blooded animals, said composition comprising an effective amount to deliver (a) at least one 5-fluorouracil selected from the group consisting of 1-(2-tetrahydrofuryl)-5-fluorouracil, 3-(2-tetrahydrofuryl)-5-fluorouracil and 1,3-bis(2-tetrahydrofuryl)-5-fluorouracil and (b) an effective amount of 3-benzoyluracil, wherein about 0.5 to about 20 moles of 3-benzoyluracil is used per mole of the 5-fluorouracil.

2. An anti-cancer composition as defined in claim 1 wherein the 5-fluorouracil is 1-(2-tetrahydrofuryl)-5-fluorouracil or 3-(2-tetrahydrofuryl)-5-fluorouracil.

3. An anti-cancer composition as defined in claim 1 which is an oral preparation.

4. An anti-cancer composition as defined in claim 1 which is a parenteral solution.

5. An anti-cancer composition as defined in claim 1 which is a suppository.

6. A method of delivering a 5-fluorouracil to a cancer sensitive to a 5-fluorouracil in a warm-blooded animal, the method comprising administering to the animal an effective amount to deliver (a) at least one 5-fluorouracil selected from the group consisting 1-(2-tetrahydrofuryl)-5-fluorouracil, 3-(2-tetrahydrofuryl-5-fluorouracil and 1,3-bis(2-tetrahydrofuryl)-5-fluorouracil and (b) 3-benzoyluracil, wherein about 0.5 to about 20 moles of 3-benzoyluracil is used per mole of the 5-fluorouracil.

7. The method of claim 6 wherein the 5-fluorouracil and 3-benzoyluracil are administered in a single preparation.

8. The method of claim 6 wherein the 5-fluorouracil and 3-benzoyluracil are administered in separate doses.

* * * * *